United States Patent
Garcia et al.

(10) Patent No.: US 9,029,598 B2
(45) Date of Patent: May 12, 2015

(54) METHODS FOR PRODUCTION OF ARGININE BIOCARBONATE AT LOW PRESSURE

(75) Inventors: Joaquin Bautista Garcia, Morristown, TN (US); Robin S. Cabanas, Somerset, NJ (US); Wilbens Josias, North Plainfield, NJ (US); Donghui Wu, Bridgewater, NJ (US)

(73) Assignee: Colgate-Palmolive Company, New York, NY (US)

( * ) Notice: Subject to any disclaimer, the term of this patent is extended or adjusted under 35 U.S.C. 154(b) by 232 days.

(21) Appl. No.: 13/515,827

(22) PCT Filed: Dec. 14, 2010

(86) PCT No.: PCT/US2010/060266
§ 371 (c)(1),
(2), (4) Date: Jun. 14, 2012

(87) PCT Pub. No.: WO2011/075472
PCT Pub. Date: Jun. 23, 2011

(65) Prior Publication Data
US 2012/0302788 A1    Nov. 29, 2012

Related U.S. Application Data

(60) Provisional application No. 61/287,843, filed on Dec. 18, 2009.

(51) Int. Cl.
| C07C 275/16 | (2006.01) |
| C07C 277/00 | (2006.01) |
| C07C 279/14 | (2006.01) |
| C07C 279/02 | (2006.01) |

(52) U.S. Cl.
CPC ............. *C07C 277/00* (2013.01); *C07C 279/14* (2013.01); *C07C 279/02* (2013.01)

(58) Field of Classification Search
CPC .............................. C07C 279/10; C07C 279/14
See application file for complete search history.

(56) References Cited

U.S. PATENT DOCUMENTS

| 3,925,543 A | 12/1975 | Donohue |
| 3,932,605 A | 1/1976 | Vit |
| 3,932,608 A | 1/1976 | Anderson et al. |
| 3,943,241 A | 3/1976 | Anderson et al. |
| 3,988,434 A | 10/1976 | Schole et al. |
| 4,011,309 A | 3/1977 | Lutz |
| 4,022,880 A | 5/1977 | Vinson et al. |
| 4,025,616 A | 5/1977 | Haefele |
| 4,042,680 A | 8/1977 | Muhler et al. |
| 4,064,138 A | 12/1977 | Saari et al. |
| 4,100,269 A | 7/1978 | Pader |
| 4,108,979 A | 8/1978 | Muhler et al. |
| 4,108,981 A | 8/1978 | Muhler et al. |
| 4,146,607 A | 3/1979 | Ritchey |
| 4,154,813 A | 5/1979 | Kleinberg |
| 4,160,821 A | 7/1979 | Sipos |
| 4,213,961 A | 7/1980 | Curtis et al. |
| 4,225,579 A | 9/1980 | Kleinberg |
| 4,259,316 A | 3/1981 | Nakashima et al. |
| 4,269,822 A | 5/1981 | Pellico et al. |
| 4,305,928 A | 12/1981 | Harvey |
| 4,335,102 A | 6/1982 | Nakashima et al. |
| 4,339,432 A | 7/1982 | Ritchey et al. |
| RE31,181 E | 3/1983 | Kleinberg |
| 4,466,954 A | 8/1984 | Ichikawa et al. |
| 4,528,181 A | 7/1985 | Morton et al. |
| 4,532,124 A | 7/1985 | Pearce |
| 4,538,990 A | 9/1985 | Pashley |
| 4,645,662 A | 2/1987 | Nakashima et al. |
| 4,656,031 A | 4/1987 | Lane et al. |
| 4,725,576 A | 2/1988 | Pollock et al. |
| 4,885,155 A | 12/1989 | Parran, Jr. et al. |
| 4,919,910 A | 4/1990 | Kurtz et al. |
| 4,997,640 A | 3/1991 | Bird et al. |
| 5,096,700 A | 3/1992 | Seibel et al. |
| 5,286,480 A | 2/1994 | Boggs et al. |
| 5,334,617 A | 8/1994 | Ulrich et al. |
| 5,370,865 A | 12/1994 | Yamagishi et al. |
| 5,639,795 A | 6/1997 | Friedman et al. |
| 5,747,004 A | 5/1998 | Giani et al. |
| 5,762,911 A | 6/1998 | Kleinberg et al. |
| 5,906,811 A | 5/1999 | Hersh |
| 5,922,346 A | 7/1999 | Hersh |
| 5,997,301 A | 12/1999 | Linden |
| 6,217,851 B1 | 4/2001 | Kleinberg et al. |

(Continued)

FOREIGN PATENT DOCUMENTS

| EP | 1135110 | 9/2001 |
| EP | 1736135 | 12/2006 |
| FR | 2547501 A1 * | 12/1984 |
| WO | WO 96/41617 | 12/1996 |
| WO | WO 97/32565 | 9/1997 |
| WO | WO 2007/008908 | 1/2007 |
| WO | WO 2009/099451 | 8/2009 |
| WO | WO 2009/100267 | 8/2009 |
| WO | WO 2009/100267 A1 * | 8/2009 |
| WO | WO 2009/100278 | 8/2009 |

OTHER PUBLICATIONS

AminoScience, L-Arginine, recovered http://www.ajinomoto.co.jp/kfb/amino /e_aminoscience/bc/amino _02.html 30 on Mar. 30, 2012.*

Acevedo et al., 2005, "The Inhibitory Effect of an Arginine Bicarbonate/Calcium Carbonate (CaviStat)-Containing Dentifrice on the Development of Dental Caries in Venezuelan School Children," J. Clinical Dentistry 16(3):63-70.

AminoScience L-Arginine recovered from http://www.ajinomoto.co.jp/kfb/amino/e_aminoscience/bc/amino_02.html on Mar. 30, 2012.

Chatterjee et al., 2005, "Bacterial Acidification and CaviStat Alkalinization of Occlusal Fissure pH," Abstract, 83rd Session of the American Association for Dental Research, Mar. 9-12, 2005, Baltimore, MD.

(Continued)

*Primary Examiner* — Paul A Zucker
(74) *Attorney, Agent, or Firm* — Rena Patel

(57) ABSTRACT

A method of producing arginine bicarbonate is provided including reacting an arginine slurry with a source of carbon dioxide gas under elevated temperature and low pressure to form a solution of at least 50% arginine bicarbonate, and recovering arginine bicarbonate from the solution.

17 Claims, 1 Drawing Sheet

(56) References Cited

U.S. PATENT DOCUMENTS

| | | | |
|---|---|---|---|
| 6,436,370 | B1 | 8/2002 | Kleinberg et al. |
| 6,488,961 | B1 | 12/2002 | Robinson et al. |
| 6,524,558 | B2 | 2/2003 | Kleinberg et al. |
| 6,558,654 | B2 | 5/2003 | McLaughlin |
| 6,805,883 | B2 | 10/2004 | Chevaux et al. |
| 6,890,497 | B2 | 5/2005 | Rau et al. |
| 2002/0081360 | A1 | 6/2002 | Burgard et al. |
| 2003/0215513 | A1 | 11/2003 | Fyhr et al. |
| 2007/0154863 | A1 | 7/2007 | Cai et al. |
| 2008/0233054 | A1* | 9/2008 | Kleinberg et al. ............. 424/48 |
| 2009/0202456 | A1 | 8/2009 | Prencipe et al. |

OTHER PUBLICATIONS

International Search Report and Written Opinion in International Application No. PCT/US09/033293, mailed Jun. 24, 2009.
International Search Report and Written Opinion in International Application No. PCT/US10/059992, mailed May 18, 2011.
International Search Report and Written Opinion in International Application No. PCT/US10/060266, mailed Mar. 14, 2011.
Kleinberg, 1999, "A New Saliva-Based Anticaries Composition," Dentistry Today 18(2):1-6.
Kleinberg, 2002, "A Mixed-Bacteria Ecological Approach to Understanding the Role of the Oral Bacteria in Dental Caries Causation: An Alternative to *Streptococcus mutans* and the Specific-Plaque Hypothesis," Critical Reviews in Oral Biological Medicine 13(2):108-125.
Machado et al., 2007, "CaviStat confetion Inhibition of Caries in Posterior Teeth," Abstract, 83rd Session of the American Association for Dental Research, Mar. 21-24, 2007, New Orleans, LA.
Packaging with Ingredient List for DenClude® (launched Dec. 2004).
Packaging with Ingredient List for ProClude® (launched Jul. 2002).
Written Opinion in International Application No. PCT/US10/059992, mailed Nov. 16, 2011.
US 5,989,525, 11/1999, Kleinberg et al. (withdrawn)

* cited by examiner

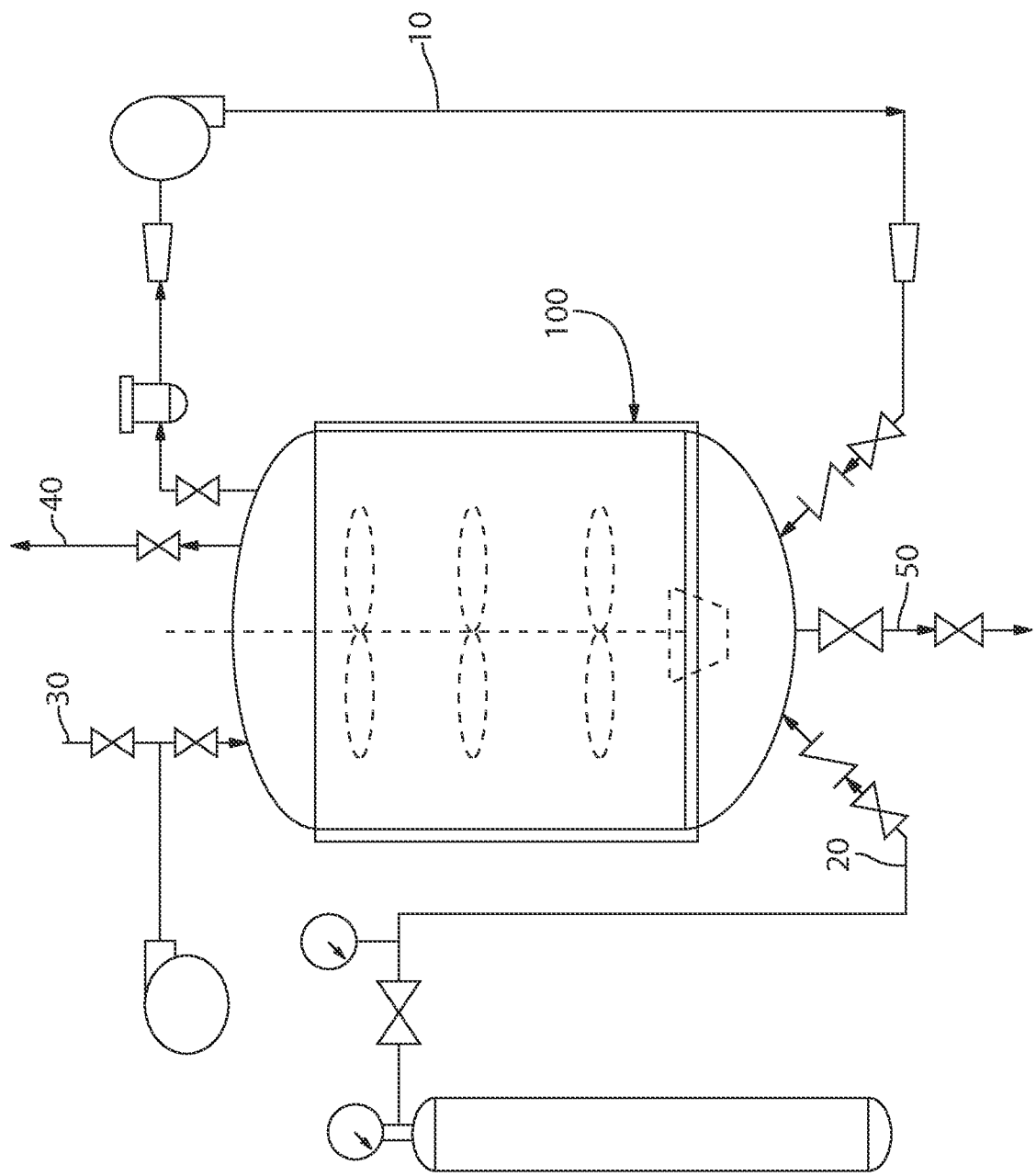

US 9,029,598 B2

METHODS FOR PRODUCTION OF ARGININE BIOCARBONATE AT LOW PRESSURE

CROSS REFERENCE TO RELATED APPLICATIONS

This application is a national stage entry under 35 U.S.C. §371 of International Patent Application No. PCT/US2010/060266, filed 14 Dec. 2010, which claims priority to U.S. Provisional Patent Application Ser. No. 61/287,843, filed on 18 Dec. 2009, which is incorporated herein by reference.

BACKGROUND

Arginine bicarbonate has use in various industrial applications, including use in personal care compositions, such as oral care compositions. For example, U.S. Pat. No. 6,524,558 describes the use of arginine bicarbonate and calcium carbonate for preventing or treating dental hypersensitivity. As the industrial requirements for arginine bicarbonate increase, so will the need for improved processes and methods for its manufacture.

PCT published application WO2009/100267 describes methods of production of arginine bicarbonate.

Arginine bicarbonate may be produced by bubbling carbon dioxide gas through a saturated arginine aqueous solution at room temperature and pressure. U.S. Pat. No. 6,217,851 describes preparing arginine bicarbonate from arginine hydroxide by bubbling carbon dioxide or by adding dry ice in excess into a solution of arginine free base. However, the efficiency of the existing process needs to be improved. The existing process is slow, requiring 24 to 48 hours to complete the reaction. Carbon dioxide has very limited solubility in water, and releasing the gas into the solution produces a maximum concentration of $1.2 \times 10^{-5}$M at room temperature and its natural partial pressure ($3.5 \times 10^{-4}$ atmosphere). The solubility of arginine in water is only 15% weight/weight at room temperature. Producing a concentrated arginine bicarbonate solution (e.g., 40%) requires the continual addition of arginine to the solution, thereby increasing production time and requiring constant monitoring of the reaction. Thus, there is a need to improve methods to manufacture arginine bicarbonate.

SUMMARY

Methods for manufacturing arginine bicarbonate. The methods represent a significant improvement over existing techniques, as concentrated solutions of about 50%, and in certain embodiments 70% w/w of arginine and bicarbonate anions may be produced in as little as about 90 to about 120 minutes (vs. about 24-48 hours to produce far lower concentrations of arginine bicarbonate using the prior art methods), followed by faster and easier recovery processes of arginine bicarbonate salt from the solution.

In one embodiment, a method of producing arginine bicarbonate including contacting carbon dioxide gas having a pressure of from 6895 Pa (1 psi) to 68947 Pa (10 psi) with a starting slurry containing arginine at a temperature of 60° C. to 80° C., to form a slurry or solution including arginine and bicarbonate anion, contacting the solution or slurry with carbon dioxide until the about slurry or solution has a concentration of arginine bicarbonate above 50% and a pH below 9, and recovering arginine bicarbonate from the solution.

In another embodiment, a process for producing arginine bicarbonate is disclosed that includes contacting an arginine water slurry in a ratio of arginine to water of 60:40 with carbon dioxide having a pressure of from 6895 Pa (1 psi) to 68947 Pa (10 psi), heating the arginine slurry to a temperature of from 60 C to 80 C for the duration of the reaction until a slurry or solution containing at least 50% arginine bicarbonate having a pH of less than 9 is formed, cooling the resulting slurry or solution to 25 C, to form a solution of arginine bicarbonate having a concentration of arginine bicarbonate of about 50% by weight.

BRIEF DESCRIPTION OF THE DRAWINGS

Certain embodiments are described in the examples that follow and illustrated in the FIGURE appended hereto.

FIG. 1 illustrates a pilot plant design for preparing arginine bicarbonate at low pressures.

DETAILED DESCRIPTION

As used throughout, ranges are used as a shorthand for describing each and every value that is within the range. Any value within the range can be selected as the terminus of the range. In addition, all references cited herein are hereby incorporated by reference in their entireties. In the event of a conflict in a definition in the present disclosure and that of a cited reference, the present disclosure controls. In addition, the compositions and the methods may comprise, consist essentially of, or consist of the elements described therein.

Unless otherwise specified, all percentages and amounts expressed herein and elsewhere in the specification should be understood to refer to percentages by weight. The amounts given are based on the active weight of the material. The recitation of a specific value herein is intended to denote that value, plus or minus a degree of variability to account for errors in measurements. For example, an amount of 10% may include 9.5% or 10.5%, given the degree of error in measurement that will be appreciated and understood by those having ordinary skill in the art. The method involves a surprisingly simple reaction to produce a high concentration of arginine bicarbonate salt by reacting a source of gaseous carbon dioxide and an arginine slurry under elevated temperature and low pressure to form an arginine and bicarbonate anion solution, wherein the salt is then recovered from solution. The initial reaction is faster than existing methods, 90 minutes vs. over 24 hours, and yields a more concentrated solution of arginine and bicarbonate anion (above 50%, and in certain embodiments 70% or above, vs. 40%).

In one embodiment, a method of producing arginine bicarbonate including contacting carbon dioxide gas having a pressure of from 6895 Pa (1 psi) to 68947 Pa (10 psi) with a starting slurry containing arginine at a temperature of 60° C. to 80° C., to form a slurry or solution including arginine and bicarbonate anion, contacting the solution or slurry with carbon dioxide until the about slurry or solution has a concentration of arginine bicarbonate above 50% and a pH below 9, and recovering arginine bicarbonate from the solution. The expression "solution or slurry" is used because as the reaction proceeds, the slurry gradually becomes a solution as more and more arginine is dissolved and arginine bicarbonate is produced. As described in more detail below, the reaction is completed when little or no arginine remains in slurry and the solution becomes clear or colorless. Accordingly, during the process of making arginine bicarbonate, the slurry containing arginine will eventually become a solution containing arginine bicarbonate.

In another embodiment, a process for producing arginine bicarbonate is disclosed that includes contacting an arginine water slurry in a ratio of arginine to water of 60:40 with carbon dioxide having a pressure of from 6895 Pa (1 psi) to 68947 Pa (10 psi), heating the arginine slurry to a temperature of from 60 C to 80 C for the duration of the reaction until a slurry or solution containing at least 50% arginine bicarbonate having a pH of less than 9 is formed, cooling the resulting slurry or solution to 25 C, to form a solution of arginine bicarbonate having a concentration of arginine bicarbonate of about 50% by weight.

In one embodiment the arginine slurry includes arginine and a solvent, in certain embodiments water, wherein the slurry is from 10% to 90% by weight arginine in free base or salt form. In a certain embodiment, the arginine water slurry is in a ratio of 60:40 w/w arginine to water. In some cases, subsequent portions of arginine may optionally be added until the ratio of arginine to water is in excess of 1.8:1, in certain embodiments in excess of 1.9:1, and in other embodiments in excess of 2.5:1.

The arginine used in certain embodiments is selected from L-arginine, D-arginine, or a mixture thereof. The arginine also can be provided by arginine hydroxide, arginine hydrochloride, or a mixture thereof.

In the methods, the carbon dioxide can be provided to the reaction as a gas under pressure as from 6895 Pa (1 psi) to 68947 Pa (10 psi), in certain embodiments from 34474 Pa (5 psi) to 68947 Pa (10 psi).

In another embodiment, the bicarbonate ion can be generated by providing sodium bicarbonate to the slurry. In another embodiment, the arginine slurry and carbon dioxide gas are maintained under elevated temperature from 90 minutes to 120 minutes. Those having ordinary skill in the art will appreciate that while the reaction can proceed for as little as 90 minutes for lab or pilot scale production of arginine bicarbonate, commercial quantity scale production of arginine bicarbonate typically will take longer, up to 5 hours. The arginine slurry and carbon dioxide therefore can be maintained under elevated temperature for 90 minutes to 5 hours, in certain embodiments from 90 minutes to 4 hours, and in other embodiments from 90 minutes to 2-4 hours, for commercial scale production.

Also described herein is a method in which the arginine slurry can first be heated to a temperature within the range of from 30 C to 80 C, in certain embodiments from 60 C to 80 C for the duration of the reaction, then cooled to a temperature within the range of from 0 C to 40 C, in certain embodiments from 0 C to 25 C after completion of the reaction. The arginine slurry used in certain embodiments has a pH of from 10 to 14. By utilizing the methods, arginine bicarbonate solutions are provided having a pH from 7 to 10, in certain embodiments from 8.3 to 8.5 (or from 7.0 to 9.0). That is, the reaction is believed to be substantially completed when the pH of the resulting solution containing the arginine bicarbonate is below 9.0. In one embodiment, the arginine bicarbonate can be recovered from the solution by evaporation or precipitation.

The present method in certain embodiments begins with the formation of an arginine slurry comprising arginine and a solvent, in certain embodiments water. As arginine free base is only slightly soluble in water at room temperature, the addition of arginine to water forms a slurry, wherein a majority of the arginine is insoluble. Any form of arginine may be utilized to form the slurry, e.g., arginine free base (in D or L form, usually L-form), or an arginine salt. It is understood that various arginine salts, e.g., hydrochloride, and pharmaceutically acceptable salts, may be substantially more soluble in water than arginine free base, and this may allow for the production of more concentrated arginine and bicarbonate anion solution. Thus, salts may be used or mixtures of free base and salts may be used in combination to form the slurry.

The slurry is produced by the addition of 10% to 90% weight of arginine to the solvent, e.g., 20% to 80%, 30% to 70%, 40% to 60%. The slurry may then be agitated to create a homogenous mixture. The initial pH of the slurry is generally 12 for arginine free base, e.g., 10 to 13.

In one embodiment, the arginine water slurry is in a ratio of 60:40 by weight. Also described herein is a method in which the slurry may be heated to 30° C. to 80° C., e.g., to 40° C. to 50° C., to 55° C., to 60° C., to 65° C., or to 70° C. to increase the solubility of the arginine in the solvent, which is in certain embodiments water. In one embodiment, the arginine water slurry is first heated from 60° C. to 80° C.

The reaction between carbon dioxide in gaseous form and water is well known in the art, wherein carbonic acid is initially formed, and disassociates into bicarbonate and hydrogen ions. The bicarbonate then further disassociates into carbonate and an additional hydrogen ion. Carbon dioxide is added to the arginine slurry in a pressurized vessel to form bicarbonate anions, resulting in a protonated arginine cation and a bicarbonate anion solution.

The equilibrium of carbon dioxide/carbonic acid and arginine is set forth in Reactions 1 and 2 below, respectively. When carbon dioxide is purged in to water, it will form carbonic acid and bicarbonate, and then react with the very basic arginine molecule to form arginine-bicarbonate, as shown in Reaction 3.

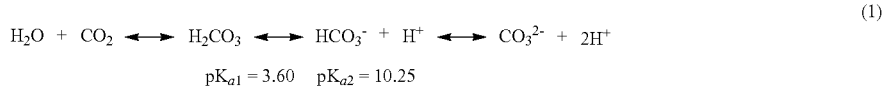

(1)

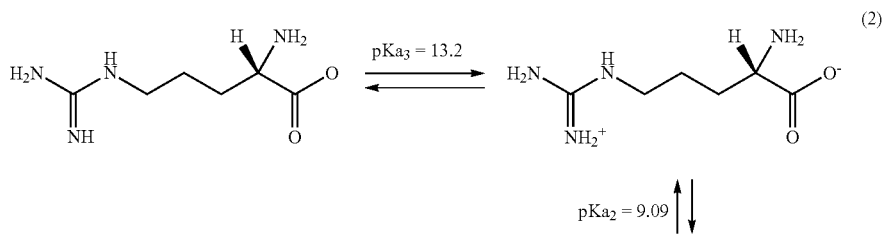

(2)

-continued

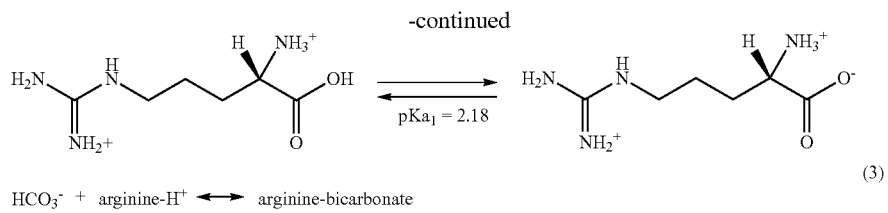

HCO$_3^-$ + arginine-H$^+$ ⇌ arginine-bicarbonate (3)

The solubility of carbon dioxide into the slurry may be increased by decreasing the temperature of the solution; however, this decreases the solubility of the arginine. Thus, it is desired that a careful balance be maintained between solubility of both components. Thus, in one embodiment, the pressurized vessel may be temperature controlled. One method of increasing the solubility of the carbon dioxide into the slurry is to provide the carbon dioxide at a lower temperature than that of a slurry, for example, by introducing carbon dioxide as dry ice, or a cooled gas. In certain embodiments, carbon dioxide gas is used. Additionally, direct cooling of the slurry may be carried out.

Also described herein is a method in which the solubility of carbon dioxide into the slurry may be increased by increasing the partial pressure of the carbon dioxide in the reaction vessel. Thus, the reaction between the carbon dioxide and the arginine slurry may occur at higher pressures outside the scope of the invention, although higher pressures are not selected for all embodiments. If a higher pressure were used, the reaction may occur from 34474 Pa (5 psi) to 1034214 Pa (150 psi), e.g., 344738 Pa (50 psi), to 413685 Pa (60 psi), to 482633 Pa (70 psi), to 551580 Pa (80 psi), to 620528 Pa (90 psi), to 689476 Pa (100 psi), to 758423 Pa (110 psi), to Pa 827371 Pa (120 psi), or to 965266 Pa (140 psi).

In one embodiment, the reaction between the arginine slurry and gaseous carbon dioxide was conducted at a pressure from 6895 Pa (1 psi) to no more than 68947 Pa (10 psi) in order to meet safety conditions of good manufacturing processes and utilize equipment that did not require a high pressure permit. In certain embodiments the pressure is from 34473 (5 psi) to 68947 Pa (10 psi).

The reaction between the arginine slurry and carbon dioxide in certain embodiments is allowed to proceed for 10 to 120 minutes. The completion of the reaction may be gauged by monitoring the presence of undissolved arginine in the slurry, as arginine in the presence of bicarbonate anions are highly soluble compared to the arginine slurry. Another method to monitor the reaction is to measure the pH of the solution in the reaction vessel directly, or sample the solution and measure its pH in an open container at room temperature.

Depending on the completion of the reaction, in certain embodiments, no solid arginine remains, and the arginine and bicarbonate anion solution is clear and colorless, and the pH is less than 9.0. Optionally, additional carbon dioxide may be added to the reaction vessel. Following the production of the arginine bicarbonate solution, the arginine bicarbonate salt may be recovered by any means known by those of skill in the art. In one embodiment, the solvent is evaporated, e.g., by heating, spray drying, or freeze drying. In another embodiment, the salt is precipitated from solution by the addition of alcohol. Alternatively, the arginine bicarbonate solution can be used as is, as a concentrated solution, without recovering the arginine bicarbonate. Upon completion of the reaction, the arginine bicarbonate solution in certain embodiments has a final concentration in excess of 50%, in certain embodiments in excess of 60%, in other embodiments, in excess of 65%, in other embodiments in excess of 70%, by weight, based on the total weight.

The present methods may be utilized to produce arginine bicarbonate in single batches, or may be used in a continuous process, such as in continuous stirred tank reactors, fluidized bed reactors, and plug flow reactors. Those skilled in the art will be capable of carrying out the methods described herein in single batch or continuous processes, using the guidelines provided herein.

In one embodiment, in order to ensure turbulent conditions that facilitate and increase the reaction speed, a compressed air blower can be utilized to recirculate the carbon dioxide gas present in the reaction vessel.

As used throughout, ranges are used as shorthand for describing each and every value that is within the range. Any value within the range can be selected as the terminus of the range. In addition, all references cited herein are hereby incorporated by reference in their entireties. In the event of a conflict in a definition in the present disclosure and that of a cited reference, the present disclosure controls. It is understood that when formulations are described, they may be described in terms of their ingredients, as is common in the art, notwithstanding that these ingredients may react with one another in the actual formulation as it is made, stored and used, and such products are intended to be covered by the formulations described.

The following examples further describe and demonstrate methods. These examples and other embodiments described herein are exemplary and not intended to be limiting in describing the full scope of compositions and methods of this invention. Equivalent changes, modifications and variations of specific embodiments, materials, compositions and methods may be made within the scope of the present invention, with substantially similar results.

SPECIFIC EMBODIMENTS

Example 1

Outside the Scope of the Invention

A slurry of pH 12 containing 50% L-arginine by weight and 50% water by weight is prepared by mixing 85 g of L-arginine with 85 g of water at room temperature. The slurry is heated to 55 C under gentle agitation. Approximately 50% of the L-arginine is determined to be dissolved by visual observation.

Example 2

Outside the Scope of the Invention

Twenty-five (25) grams of dry ice particles are added to the slurry produced in EXAMPLE 1, and the mixture is transferred to a pressurized vessel. The dry ice is allowed to sublime in order to purge atmospheric air from the vessel, and then the vessel is sealed. Pressure in the vessel is allowed to increase to 551580 Pa (80 psi), and the solution is maintained under pressure for 3 minutes. The vessel is opened, and a small amount of unreacted arginine is observed at the bottom of the vessel.

Example 3

Outside the Scope of the Invention

The solution of EXAMPLE 2 is stirred with a spatula to make a suspension. Ten (10) grams of dry ice is added to the vessel, and the vessel is sealed. The pressure is allowed to increase to, and maintained at 620528 Pa (90 psi). The vessel is opened after 3 minutes, and a thick clear colorless solution is observed without precipitation. The solution had dropped to 12 C producing an arginine bicarbonate solution of 60% concentration, and a final pH of 8.8. Arginine bicarbonate salt is recovered by freeze drying.

Example 4

A plant scale up process as illustrated in FIG. 1 is designed to produce arginine bicarbonate. Process conditions are determined in order to produce arginine bicarbonate at a low capital investment based on plant suitable equipment availability and safety conditions that did not require a high pressure permit.

85% pure L-arginine and deionized water are added via lines 25 and 30 respectively to a 50 gallon vessel 100 equipped with a mixer. $CO_2$ gas is added via line 20 to the slurry and allowed to react. The initial temperature of the reaction vessel is increased from about 60° C.-65° C. (140° F.-150° F.) to about 70° C.-75° C. (158° F.-167° F.) and then cooled to a final temperature of about 25° C.-30° C. (77° F.-86° F.). The pressure in the reaction vessel is maintained at 68947 Pa (10 psi) based on lower inlet pressure. A blower connected to line 10 is used to recirculate the carbon dioxide gas in order to increase the reaction speed. A vent 40 also is provided.

The reaction is allowed to proceed and the estimated batch completion time is about 89-91 minutes. The final pH of the arginine bicarbonate solution is from about 8.3 to about 8.5. The amount of carbon dioxide gas required for full 1:1 conversion of 60 kg of L-arginine water slurry is about 15.15 kg. An arginine bicarbonate solution of 70.65% by weight is obtained via product line 50.

This example illustrates a low pressure, high temperature economical process of preparing an arginine bicarbonate solution in about 70% yield by using equipment that did not require a high pressure permit.

What is claimed is:

1. A method of producing arginine bicarbonate comprising:
    contacting carbon dioxide gas a at a partial pressure of from 6895 Pa (1 psi) to 68947 Pa (10 psi) with a starting slurry containing arginine at a temperature of 60° C. to 80° C. to form a slurry or solution including arginine and bicarbonate anion;
    contacting the slurry or solution with carbon dioxide until the slurry or solution forms a solution having a pH below 9; and
    recovering arginine bicarbonate from the solution.
2. The method of claim 1 wherein the arginine slurry comprises arginine and a solvent wherein the slurry comprises 10% to 90% by weight arginine in free base or salt form.
3. The method of claim 1, wherein the solvent is water.
4. The method of claim 1, wherein the arginine water slurry is in a ratio of 60:40 w/w arginine to water.
5. The method of claim 1, wherein the arginine is selected from the group consisting of L-arginine, D-arginine, and mixtures thereof.
6. The method of claim 1, wherein the arginine is selected from the group consisting of arginine hydroxide, arginine hydrochloride, and mixtures thereof.
7. The method of claim 1, wherein the carbon dioxide gas has a partial pressure from 34474 Pa (5 psi) to about 68947 Pa (10 psi).
8. The method of claim 1, wherein the arginine slurry and carbon dioxide are maintained under said partial pressure for 90 minutes to 5 hours.
9. The method of claim 1, wherein the arginine slurry is first heated to a temperature of from 30 C to 80 C for the duration of the reaction, then cooled to a temperature of from 0 C to 40 C after the slurry or solution has a pH below 9.0.
10. The method of claim 1, wherein the arginine slurry is first heated a temperature of from 60 C to 80 C for the duration of the reaction, then cooled down to a temperature of from 40 C to 25 C.
11. The method of claim 1, wherein the arginine slurry has a pH of 10 to 14.
12. The method of claim 1, wherein the arginine bicarbonate solution has a pH of from 7 to 9.
13. The method of claim 1, wherein the arginine bicarbonate solution has a pH from 8.3 to 8.5.
14. The method of claim 1, wherein the arginine bicarbonate is recovered from the solution by evaporation or precipitation.
15. The method of claim 1, wherein sodium bicarbonate is provided to the slurry.
16. The method of claim 1, wherein the arginine bicarbonate is produced under turbulent conditions.
17. A process for producing arginine bicarbonate comprising:
    contacting an arginine water slurry in a ratio of arginine to water of 60:40 with carbon dioxide at a partial pressure of from 6895 Pa (1 psi) to 68947 Pa (10 psi);
    heating the arginine slurry to a temperature of from 60 C to 80 C for the duration of the reaction until a slurry or solution containing at least 50% arginine bicarbonate having a pH of less than 9 is formed; and
    cooling the resulting slurry or solution to 25 C, to form a solution of arginine bicarbonate having a concentration of arginine bicarbonate of 50% by weight.

* * * * *